United States Patent [19]

Bardy et al.

[11] Patent Number: 5,174,288
[45] Date of Patent: Dec. 29, 1992

[54] METHOD AND APPARATUS FOR CARDIAC DEFIBRILLATION

[75] Inventors: Gust H. Bardy, Seattle, Wash.; Peter J. Pohndorf, Stillwater, Minn.

[73] Assignee: Medtronic, Inc., Minneapolis, Minn.

[21] Appl. No.: 621,112

[22] Filed: Nov. 30, 1990

[51] Int. Cl.$^5$ .............................................. A61N 1/39
[52] U.S. Cl. .................................. 128/419 D; 128/786
[58] Field of Search ........................... 128/419 D, 786

[56] References Cited

U.S. PATENT DOCUMENTS

| | | | |
|---|---|---|---|
| Re. 27,652 | 5/1973 | Mirowski et al. | 128/419 D |
| 3,857,398 | 12/1974 | Rubin | 128/419 D |
| 3,942,536 | 3/1976 | Mirowski et al. | 128/419 D |
| 4,161,952 | 7/1979 | Kinney et al. | 128/786 |
| 4,291,699 | 9/1981 | Geddes et al. | 128/419 D |
| 4,355,646 | 10/1982 | Kallok et al. | 128/786 |
| 4,481,953 | 11/1984 | Gold et al. | 128/786 |
| 4,499,907 | 10/1982 | Kallok et al. | 128/786 |
| 4,641,656 | 2/1987 | Smits | 128/419 D |
| 4,708,145 | 11/1987 | Tacker, Jr. et al. | 128/419 D |
| 4,727,877 | 3/1988 | Kallok | 128/419 D |
| 4,932,407 | 6/1990 | Williams | 128/419 D |

OTHER PUBLICATIONS

Electrode Catheter for Transvenous Defibrillation by Ewy et al., published in Medical Instrumentation, vol. 10, No. 3, May-Jun., 1976.

*Primary Examiner*—Kyle L. Howell
*Assistant Examiner*—Scott M. Getzow
*Attorney, Agent, or Firm*—Harold R. Patton; Reed A. Duthler

[57] ABSTRACT

A system of implantable defibrillation leads, and methods for their use. Each lead is provided with an elongated defibrillation electrode surface, made up of a plurality of electrode coils. Each electrode coil is mutually insulated from other electrode coils, and coupled to a separate electrical connector. In some embodiments, the electrical coils are interwound, and each extend along the length of the electrode surface. In other embodiments, the electrode coils are arranged sequentially, and each extend over only a portion of the elongated electrode surface. In use, the individual electrode coils or combination of coils may be selected to define an optimal electrode length and/or surface area for use in conjunction with particular multiple electrode defibrillation system. In addition, the ability to select between individual ones of the plurality of the electrode coils also provides the possibility for repair the defibrillation lead system after implant without the necessity of removing and replacing the defibrillation leads.

11 Claims, 4 Drawing Sheets

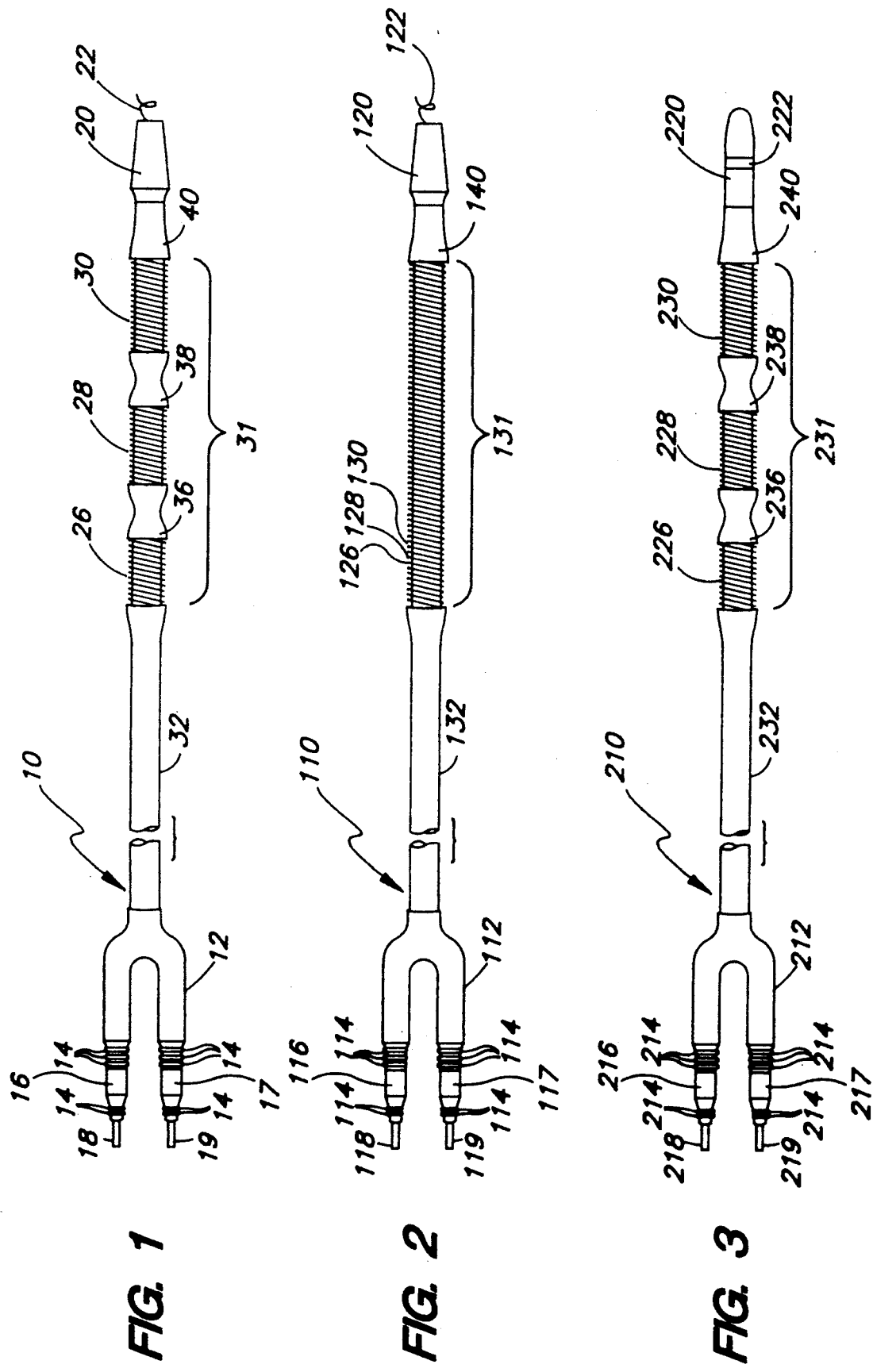

METHOD AND APPARATUS FOR CARDIAC DEFIBRILLATION

BACKGROUND OF THE INVENTION

This invention relates generally to implantable electrode leads and implantable stimulators, and more particularly to implantable defibrillation electrode leads and to implantable defibrillators.

Over the past 20 years, there has been substantial work toward developing a practical, implantable defibrillator. However, several significant problems still remain. Early conceptions of implantable defibrillators, such as disclosed in U.S. Pat. No. R. 27,652 by Mirowski et al., envision a system employing a ventricular endocardial electrode and a plate electrode, mounted directly to the heat, subcutaneously, or applied to the skin. However, it was recognized early on that a totally transvenous system would be desirable in order to simplify the use of implantable defibrillators. One such system is suggested in U.S. Pat. No. 3,942,536 by Mirowski et al., which discloses a transvenous lead having electrodes intended for location in the right ventricular apex and superior vena cava. Such systems were eventually tested in human beings with some success. However, currently available commercial versions of implantable defibrillators generally employ epicardial patch electrodes alone or in conjunction with transvenous electrodes.

While systems employing epicardial patch electrodes are workable, a thoracotomy is required in order to apply the epicardial electrode or electrodes. It is generally believed that it would be highly desirable to produce an implantable defibrillator which would entirely avoid the necessity of a thoracotomy, and there has been substantial work directed toward such systems, as disclosed in U.S. Pat. No. 4,727,877 issued to Kallok and U.S. Pat. No. 4,708,145 issued to Tacker et al. Both Tacker et al. and the Kallok patents disclose the use of a transvenous, two-electrode lead in combination with a subcutaneous patch electrode.

Transvenous ventricular defibrillation electrodes are also shown in the above-cited Mirowski patents and in the Tacker and Kallok patents cited above. Other endocardial defibrillation electrodes are disclosed in U.S. Pat. No. 4,481,953 issued to Gold et al., U.S. Pat. No. 4,161,952 issued to Kinney et al., and U.S. Pat. No. 4,641,656 issued to Smits. The Kinney, Smits and Kallok patents also disclose transvenous defibrillation electrodes intended for use in or adjacent to the coronary sinus.

U.S. Pat. No. 4,392,407 issued to Williams et al. and co-pending, commonly assigned application Ser. No. 284,957 by Mehra and Ser. No. 284,955 by Bardy, both filed Dec. 15, 1988 disclose multiple electrode systems employing subcutaneous patch electrodes, coronary sinus/great vein electrodes, and ventricular endocardial electrodes.

U.S. Pat. No. 4,355,646 issued to Kallok shows endocardial defibrillation leads employing multiple electrodes for location in the right ventricle, each of the electrodes being coupled to a different electrical connector. In use, the ventricular electrodes of the Kallok lead are coupled together during delivery of a defibrillation pulse, and the pulse is delivered between the paired ventricular electrodes and corresponding pair of electrodes located in the superior vena cava. This is the same endocardial electrode system as disclosed in the above-cited Tacker patent. A similar electrode lead is disclosed in U.S. Pat. No. 4,291,699 issued to Geddes et al., in which the two ventricular electrodes are tied together during delivery of a defibrillation pulse, and also used for sensing impedance of the blood within the ventricle. Yet another use of a lead as disclosed in the Kallok et al. patent is set forth in U.S. Pat. No. 4,499,907, which employs the two ventricular electrodes coupled together during delivery of a defibrillation pulse, and also employs the two ventricular electrodes as bipolar pair for sensing the electrical signals indicative of heart contractions, in the fashion of a normal, bipolar pacemaker.

An additional multi-electrode ventricular defibrillation lead is disclosed in U.S. Pat. No. 3,857,398 issued to Rubin. The two ventricular electrodes in the Rubin lead are employed for ventricular pacing and sensing of heart beats. One of the ventricular electrodes is used in conjunction with an atrial electrode for delivery of defibrillation pulses.

SUMMARY OF THE INVENTION

The present invention is directed towards defibrillation leads and defibrillation lead systems which allow for reconfiguration of the defibrillation electrode arrangement, without the necessity of repositioning or replacing the defibrillating leads. The invention also provides a method for repair and correction of defects which may arise in the lead system, either due to mechanical or electrical failure of the leads themselves, or to a change in the patient's underlying condition.

In some of the leads described, the defibrillation electrode surface is defined by a series of discreet electrode surfaces arranged end-to-end, each of the electrode surfaces coupled to a different electrical connector. This allows for an adjustment of the effective length of the defibrillation electrode surface, which is particularly valuable in conjunction with electrode systems employing coronary sinus/great vein electrodes in conjunction with right ventricular electrodes. The ability to adjust the effective length of the electrode surfaces is also of value in tailoring the electrode systems to the heart anatomy of the particular patient in which the leads are implanted.

Other embodiments of leads for use in conjunction with the present invention include multiple electrode coils, interwound to form a multipolar electrode coil. In this lead embodiment, failure of one of the individual electrode coils can be corrected without removal of the lead by connecting another of the electrode coils, to replace the coil determined to be defective. This design also allows for selection of one, two or all of the electrode coils for use in delivery of defibrillation pulses, thus allowing for variation in the overall actual surface area of the electrode. In situations in which higher than normal defibrillation energies are to be employed, this also provides a benefit by providing parallel circuit paths extending from the implanted defibrillator to the electrode surfaces.

Selection of electrode coils or electrode surfaces may be accomplished by means of a mechanical switching apparatus at the time of implant or at pulse generator replacement. Selection of electrode coils or surfaces may also be accomplished electronically by means of switching circuitry within the implantable cardioverter to which the leads are coupled, in response to telemetry control signals from an external programmer. In such case, reconfiguration of the electrode system would not require surgical intervention.

BRIEF DESCRIPTION OF THE DRAWINGS

FIG. 1 is a plan view of a ventricular electrode according to the present invention.

FIG. 2 is a plan view of a second embodiment of a ventricular electrode according to the present invention.

FIG. 3 is a plan view of a coronary sinus/great vein electrode according to the present invention.

FIG. 5b is a cross sectional view through the heart, illustrating the location of the electrode illustrated in FIG. 3, in an electrode system as illustrated in FIG. 5a.

DETAILED DESCRIPTION OF THE INVENTION

Figure 4:
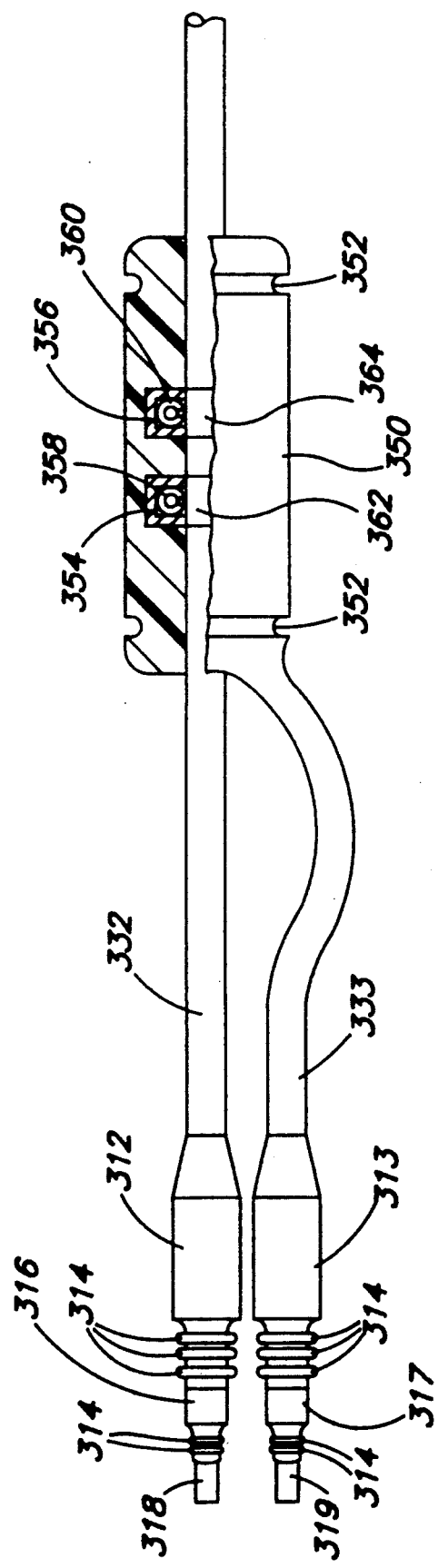
FIG. 4 is a cutaway view of a coil selecting apparatus for use with the leads illustrated in FIGS. 1 through 3.

FIG. 1 is a top, plan view of a right ventricular defibrillation lead according to the present invention. The lead might also be employed in the right atrium, or in other locations within the heart accessible through the venous or arterial system. However, its normal location is anticipated to be in the right ventricle.

The lead 10 is provided with a bifurcated multipolar electrical connector assembly 12, which includes two conductive electrode pins 18 and 19, and two conductive electrode rings 16 and 17, all of which are mutually insulated from one another. Fluid sealing between the electrode pins and electrode rings and sealing of the lead within the connector of implantable defibrillator is provided by sealing rings 14. The overall configuration of connector assembly 12 is that of a bifurcated connector, each having a connector pin and a connector ring, each arm of the bifurcated connector having a connector assembly which generally corresponds to the requirements of the IS-1 international standard for implantable pacemaker leads. However, any other multipolar connector configuration might also be used.

Extending proximally from connector assembly 12 is an elongated insulative sheath 32, which surrounds four mutually insulated electrical conductors (not visible). Each of the four electrical conductors extends from one of the connector pins and connector rings to one of the electrodes located along the distal portion of the lead. These electrodes include three electrodes coils 26, 28 and 30, separated by insulative segments 36 and 38, and a helical electrode 22 adapted to be screwed into heart tissue, to hold the tip assembly 20 adjacent to heart tissue. An appropriate structure for this electrode and a method for rotation of the helix is disclosed in U.S. Pat. No. 4,106,512 by Bisping, issued Aug. 15, 1978 and incorporated herein by reference in its entirety. The electrode head 20 is spaced from electrode 30 by an insulative sleeve 40.

It should be noted that the insulative sheath 32, and the insulative sleeves 36, 38 and 40 are shown as mounted surrounding the electrode coils 26, 28 and 30 at their proximal and distal ends. The provision of insulative sleeves between the individual electrode coils and mounted around the coils at their proximal and distal ends assists in focusing the electrical field generated by each coil, and concentrating it, in the immediate vicinity of the electrodes, around the electrode surface. This assists in preventing excessive propagation of the electrical field generated by individual electrode coils, and allows adjustment of the defibrillation electrode, by selectively disconnecting one or more of electrode coils 26, 28 and 30. Connection and disconnection of electrode coils may be accomplished manually by means of a switching apparatus as illustrated in FIG. 4 or electronically by means of switching circuitry within the implantable defibrillator.

For example, in the context of an electrode system employing a right ventricular and coronary sinus/great vein electrode as illustrated in the above-cited Williams et al. patent, it is desirable that the proximal ends of the two electrodes are not too closely spaced. A ventricular electrode extending from an area adjacent the right ventricular apex, to a point adjacent the tricuspid valve is appropriate in such a system. Depending upon the size of the patient's heart, this may be provided by electrode coils 28 and 30 together, or by electrode coil 30 alone.

In contrast, in an electrode system employing a right ventricular electrode in conjunction with a subcutaneous plate, it is desirable to employ an electrode which extends further proximally within the heart. In this case, the electrode system may advantageously employ electrode coils 28 and 30 together in patients with small hearts, or may employ all three electrodes 26, 28 and 30.

Figure 5A:
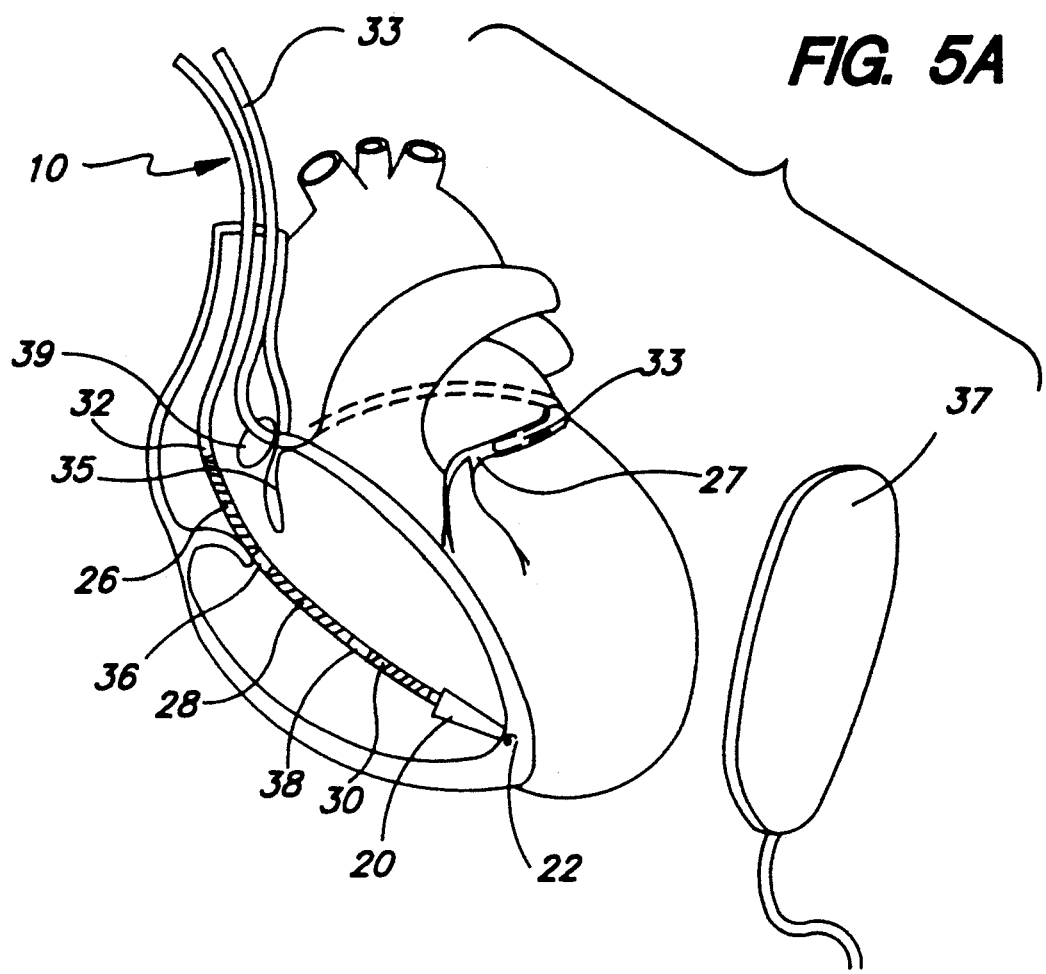
FIG. 5a is a side, cutaway view of the human heart, illustrating the use of the electrodes illustrated in FIGS. 1 and 3 in the context of an implanted defibrillation electrode system, also employing a subcutaneous plate.
Figure 6A:
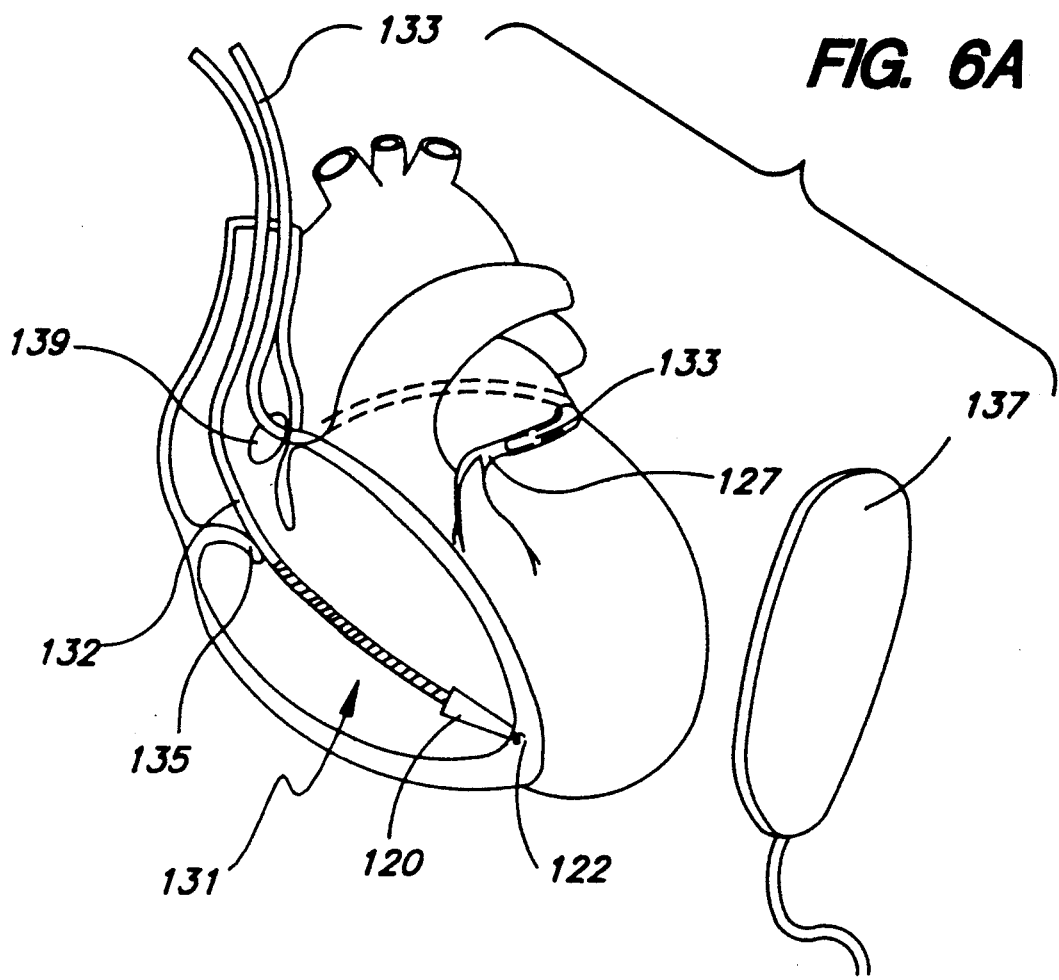
FIG. 6a is a side, cutaway view of the heart illustrating the use of an electrode as illustrated in FIG. 2, in the context of an implantable electrode system also employing a subcutaneous plate and a coronary sinus lead.

It is anticipated that the electrode of FIG. 1 may be implanted in an electrode system comprising a right ventricular lead, a coronary sinus/great vein lead, and a subcutaneous plate as illustrated in FIGS. 5a and 6a. This system will allow switching between the electrode configurations discussed above. It is also possible to employ all three leads simultaneously, in which case if pulses are delivered between the coronary sinus and right ventricular electrodes, adequate spacing between the proximal ends of these electrodes would be desirable. In systems as illustrated in FIG. 5a, for example, electrodes 28 and 30 would be employed in delivering pulses between the right ventricular electrodes and the coronary sinus electrodes. However, in multiple electrode systems in which the coronary sinus and the right ventricular electrodes are sequentially paired with a subcutaneous electrode or in which the coronary sinus and right ventricular electrodes are simultaneously paired with a subcutaneous electrode, all three electrode coils 26, 28 and 30 would be employed to deliver the cardioversion or defibrillation pulses.

Simultaneous and sequential pulse regimens as discussed above are all disclosed in the above-cited Williams U.S. Pat. No. 4,932,407, issued Jun. 12, 1990, incorporated herein by reference in its entirety. Also disclosed and claimed within the Williams patent is an additional multi-electrode system for delivering sequential defibrillation or cardioversion pulses to the heart, in which two spaced electrodes are located within the coronary sinus and great vein, respectively. Pulses are sequentially delivered a between a right ventricular electrode located adjacent the apex of the heart and each of the coronary sinus and great vein electrodes. In the context of an electrode system such as this, it is anticipated that only electrode coil 30 would be employed on the ventricular lead 10.

FIG. 5a illustrates the lead of FIG. 1, as it is implanted in the heart, in conjunction with a coronary sinus/great vein lead 33 and a subcutaneous electrode 37. The ventricular lead 10 is passed through the venous system, through the superior vena cava, right atrium and tricuspid valve, until its distal end is adjacent to the right ventricular apex. Helical electrode 22 is then screwed into the myocardium of the right ventricular apex, anchoring the lead in place. As illustrated, all numbered components of the lead 10 correspond to the identically numbered components in FIG. 1. In this view, it can be seen that electrode coils 28 and 30, in a normal size heart, are located completely within the right ventricle, while electrode coil 26 is located in the tricuspid valve/atrial area. The coronary sinus/great vein lead 33 is shown entering the opening of the coronary sinus 39, and passing around the heart, so that its distal end is located in the great cardiac vein 31, adjacent the left atrial appendage.

In simultaneous pulse regimens, pulses would be applied sequentially between, for example, the coronary sinus and right ventricular electrodes and between the right ventricular electrode and the subcutaneous electrode. Alternatively, pulses might sequentially be applied between the coronary sinus and subcutaneous electrodes and then between the subcutaneous and right ventricular electrodes. In the first configuration, which employs pulses delivered between the coronary sinus and right ventricular electrodes, only the distal one or two electrodes on the right ventricular lead are likely to be employed. In sequential systems in which pulses are not delivered between the coronary sinus and right ventricular electrodes, all three ventricular electrodes will likely be employed.

In simultaneous pulse regimens, the same basic considerations apply. In the case of a simultaneous pulse regimen in which the coronary sinus and subcutaneous electrodes are electrically coupled to one another and a pulse is delivered between these coupled electrodes and the right ventricular electrode, only the distal one or two electrode coils on the ventricular lead should be active, in order shorten effective length of the right ventricular defibrillation electrode. In contrast, if the right ventricular and coronary sinus electrodes are electrically coupled together and a pulse is delivered between these two electrodes and the subcutaneous patch electrode, then spacing between the right ventricular and coronary sinus electrodes becomes less important, and it is likely that all three ventricular electrode coils would be employed.

FIG. 2 is side, plan view of a second embodiment of a defibrillation electrode intended for use primarily in the ventricle. Like the electrode illustrated in FIG. 1, above, it might also be used in the atrium, or in other chambers of the heart accessible through the arterial or venous system. This lead, in use, may be substituted for any prior art transvenous defibrillation lead of the type comprising an elongated electrode. As illustrated, the lead is provided with a helical electrode 122 at its distal tip, intended for implantation in the heart tissue, similar to the electrode 22, discussed above in conjunction with FIG. 1. However, if the lead of FIG. 2 were to be adapted for use in the coronary sinus, the electrode head 120 and the helical electrode 122 could be dispensed with, or replaced with a simple ring or tip electrode.

The lead of FIG. 2 is provided with a connector assembly which corresponds to connector assembly 12, illustrated in FIG. 1. The connector assembly 112 includes connector pins 118 and 119, connector rings 116 and 117, and is provided with insulative sealing rings 114 which function as fluid seals. Each of the connector rings 116 and 117 and connector pin 118 are coupled to one of three electrode coils 126, 128 and 130, which together define an elongated electrode surface 131 extending for at least four cm, or corresponding roughly to the distance from the right ventricular apex to the tricuspid valve. In embodiments intended for use in the coronary sinus/great vein, the electrode surface 133 would extend for about 4-8 cm. Electrode coils 126, 128 and 130 are wound parallel to but spaced from one another, and the conductors connecting connector pins 118 and 119 and connector ring 116 to the coil electrodes 126, 128 and 130 are mutually insulated from one another, so that each individual electrode coil may be separately coupled to an implantable defibrillator. As discussed above in conjunction with FIG. 1, insulative sheaths 132 and 140 overlap the proximal and distal ends of the electrode coils 126, 128 and 130. Helical electrode 122 is coupled to connector pin 119, is used for cardiac pacing and sensing functions, and serves to anchor the electrode head 120 to the heart tissue.

In use, in response to detection of fault with the electrode coil currently in use, for example, a fracture in the electrode coil or conductor leading to an excessively high impedance, the implantable defibrillator to which the lead 110 is attached may switch connections, and select one or more presently unconnected electrode coils as a substitute for the damaged coil or conductor. Alternatively, a break in the electrode coil or conductor leading to the electrode coil might be detected via x-ray, or via testing of the lead following detected malfunction of the implanted defibrillator to which the lead is attached. In this case, selection of electrode coil may be accomplished manually using the apparatus illustrated in FIG. 4, or may be accomplished by means of electronic switching circuitry within the implanted defibrillator in response to telemetered commands from an external programmer.

Figure 6B:
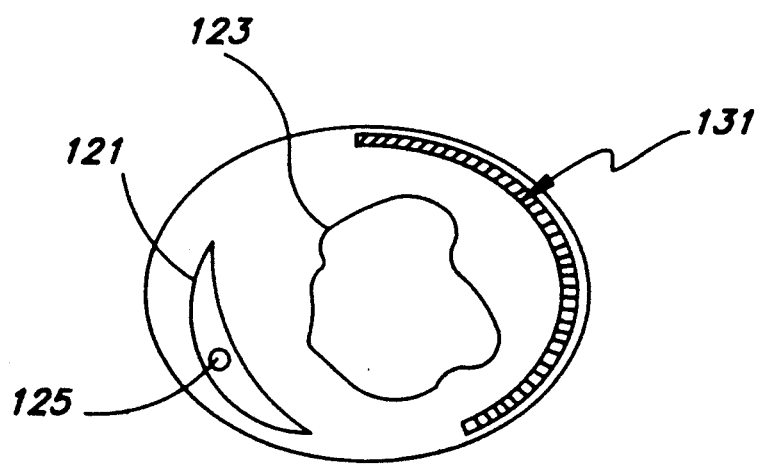
FIG. 6b is a cross sectional view through the heart illustrating the location of an electrode having a multipolar electrode coil as illustrated in FIG. 2, but located in the coronary sinus and great vein of the heart.

FIGS. 6a and 6b show intended locations for the ventricular lead illustrated in FIG. 2, and a corresponding coronary sinus/great vein embodiment of the lead, in which the helical electrode is dispensed with. In FIG. 6a, the lead 110 is shown passing through the superior vena cava, the right atrium and tricuspid valve. Its distal end is located in the right ventricular apex, with helical electrode 122 serving to anchor the lead in place. As illustrated, the elongated electrode surface 131 is located entirely within the right ventricle. In embodiments in which pulses are not delivered between a right ventricular and a coronary sinus electrode, a longer electrode surface may be appropriate. All other numbered elements of the lead correspond to those illustrated in FIG. 2. A coronary sinus/great vein lead 133 is shown entering the opening of the coronary sinus 139, and passing around the heart, terminating in the great vein 127 adjacent to left atrial appendage. A subcutaneous patch electrode 137 is also illustrated. This overall electrical configuration corresponds to an electrode configuration illustrated in the above-cited Williams patent.

FIG. 6b shows a transverse section through the heart, illustrating the location of a corresponding embodiment to the lead of FIG. 1, adapted for use in the coronary sinus/great vein. In this case, the elongated defibrillation electrode 131 is shown as extended around the heart, located within the coronary sinus and great vein. A right ventricular lead 125 is illustrated in the right ventricular cavity 121. In this view it is clear that the left ventricular cavity 123 and the majority of the left ventricular mass is located between electrode 131 and the right ventricular lead 125.

FIG. 3 shows a side, plan view of a lead generally corresponding to that illustrated in FIG. 1, but adapted for use in the coronary sinus. A similar modification, as discussed above, may be employed to adapt the lead of FIG. 2 for use in the coronary sinus/great vein region of the heart.

Like the lead of FIG. 1, the lead is provided with a bifurcated connector assembly 212, which includes connector pins 218 and 219 and connector rings 216 and 217. The connector assembly 212 is also provided with sealing rings 214 which function as fluid seals. Connector rings 216 and 217 and connector pin 218 are each coupled to one of electrode coils 226, 228 and 230 by means of mutually insulated conductors. Insulative sheaths 232, 236, 238 and 240 overlie the proximal and distal ends of electrode coils 226, 228 and 230, and function as discussed above in conjunction with FIG. 1. At the distal end of the lead is a flexible electrode head 220 which may carry an optional ring electrode 222, coupled to connector pin 219, for use in sensing of heart activity, and depending upon its location in the coronary sinus/great vein region, for cardiac pacing as well.

Figure 5B:
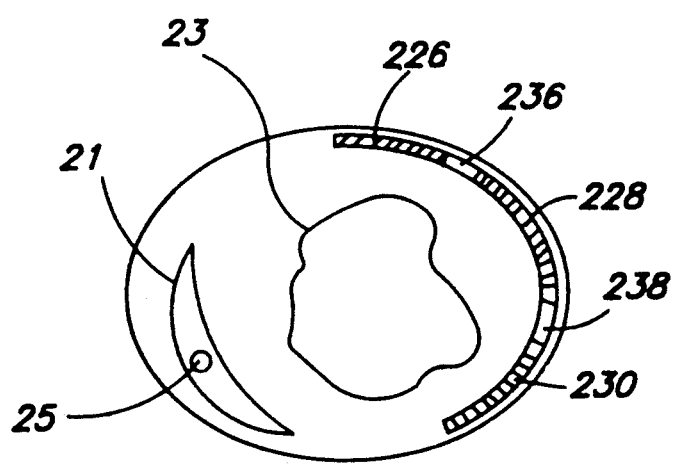

FIG. 5b illustrates the location of electrodes 226, 228 and 230 in the coronary sinus and great vein of a human heart, when the lead of FIG. 3 is implanted. The cross section through the heart illustrated in FIG. 5b also illustrates the cross section of a ventricular endocardial lead, 27. Lead 27 may correspond to lead 10 illustrated in FIG. 1, in a preferred embodiment of practicing the invention.

In use, the physician or the implantable defibrillator to which the lead is attached selects which of electrodes 226, 228 and 230 are to be used during delivery of defibrillation pulses. For example, if the defibrillation system includes a right ventricular lead and a subcutaneous patch, as illustrated in FIG. 5a, all three electrodes 226, 228 and 230 may be used during delivery of a defibrillation pulse between the coronary sinus lead and the subcutaneous patch. However, especially in smaller hearts, it may be desirable to disconnect the more proximal electrode coil 226, when delivering impulses between a right ventricular lead and the lead illustrated in FIG. 3, in order to assure that the proximal end of the activated electrodes are adequately spaced from one another. In the event that the electrodes on the right ventricular and coronary sinus leads are coupled together during delivery of a defibrillation pulse, it is anticipated that all three electrode coils 226, 228, and 230 would be used simultaneously.

In a preferred embodiment of practicing the invention, the lead of FIG. 1 may be combined with the lead of FIG. 3 in a multiple lead system as illustrated in FIG. 5a. In this case, precise tailoring of the effective electrode lengths for each pulse delivery regimen is possible. Selection of the effective electrode lengths may be accomplished automatically by an implanted defibrillator or may be accomplished manually by the physician at the time of implant, using the electrode selector illustrated in FIG. 4.

The leads of FIG. 1 and FIG. 3 are particularly advantageous in the event that the physician desires to employ a totally transvenous electrode system, consisting only of the coronary sinus and ventricular leads, and yet wishes to retain the flexibility to employ sequential pulse defibrillation. Because an electrode system comprising the leads of FIG. 1 and FIG. 3 provides six individually selectable electrode coils, electrode coils are available to accomplish a multiple pulse defibrillation regimen using only two leads. For example, the multiple pulse defibrillation regimen claimed in the above-cited Williams patent may be practiced using the distal electrode coil 30 of the lead illustrated in FIG. 1, and electrode coils 226 and 230 of the lead illustrated in FIG. 3. Pulses may be applied between electrode coils 30 and 226, and between electrode coils 30 and 230 sequentially. Other possible pulse configurations are also available, pairing individual electrodes on the lead illustrated in FIG. 1, with individual electrodes on the lead illustrated in FIG. 3. For example, electrode coil 26 of the lead of FIG. 1 might be paired with electrode coil 230 of the lead of FIG. 3 for delivery of a first pulse, and electrode coil 226 of the lead of FIG. 3 might be paired with electrode coil 20 of the lead of FIG. 1 to deliver the second pulse of a multiple pulse regime. Other variations are also possible employing the leads of FIG. 1 and FIG. 3 in conjunction with subcutaneous electrodes or other transvenously located electrodes.

The leads illustrated in FIGS. 1, 2 and 3 may also be used with an implantable defibrillator which has the capability of automatically selecting between the multiple electrode surfaces on leads as illustrated in FIGS. 1, 2 and 3. In such a device, the implantable defibrillator employs impedance sensing apparatus to detect faults in the electrode system, and corrects these faults automatically by selection of different combinations of the electrodes illustrated. This apparatus may be employed in conjunction with the leads as illustrated in FIGS. 1 and 3, to select a more optimal lead configuration in the event that one or more of the electrode coils or leads fails. It may also be employed in conjunction with the lead of FIG. 2, to correct detected short and open circuits.

Such a device disclosed may be provided with means for automatically selecting between the electrode coils on the leads, depending upon the overall system configuration (e.g. 2 electrode single pulse, multi-electrode simultaneous or sequential) selected by the physician. However, the leads of FIGS. 1 through 3 may also advantageously be employed in conjunction with implantable defibrillators having substantially lesser capabilities. In this case, it is anticipated that the leads would be employed with a manual electrode selector as illustrated in FIG. 4 may be used with any one of the leads illustrated, and is intended to replace the bifurcated connector assemblies 12, 112 and 212 illustrated in FIGS. 1, 2 and 3, respectively.

Electrode selector of FIG. 4 also takes the general form of a bifurcated connector. The connector includes two bipolar connector assemblies 312 and 313. Connector assembly 312 is provided with a connector pin 318, a connector ring 316, and insulative sealing rings 314, all of which perform identical functions to those discussed in conjunction with the connectors illustrated in FIGS. 1 through 3. Similarly, the second connector assembly 313 is provided with a second connector pin 319, a second connector ring 317 and insulative sealing rings 314. In use, it is anticipated that the connector pin 318 will be coupled to the distal electrode (22, 122, 222), and that the connector ring 316 will be coupled to one of the electrode coils. The other two electrode coils are individually coupled to connector rings 362 and 364, mounted around insulative sheaths 332. Insulative sheath 332 corresponds to insulative sheaths 32, 132 and 232 in FIGS. 1, 2 and 3 respectively, and extends until the proximal most end of the electrode coil. Connector assembly 313 is connected by an insulative sheath 333 to a slidable electrode selector 350. Electrode selector 350 is preferably fabricated of a pliant, insulative plastic such as silicone rubber and is provided with two annular grooved metal ferrules 354 and 356, each of which are coupled to one of connector pin 319 and connector ring 317. Mounted within ferrules 354 and 356 are garter springs 358 and 360, which provide electrical contact to connector rings 362 and 364. By sliding electrode selector 350 relative to insulative sheath 332, either one or both of the defibrillation electrode coils coupled to connector rings 362 and 364 may be coupled to connector surfaces 317 and 319. Alternatively, the electrode selector 350 may be positioned such that neither of the electrodes to which connector rings 362 and 364 are connected are selected.

In conjunction with leads as illustrated in FIGS. 1 and 3, it is anticipated that the distal most electrode coil 30 or 230 will be permanently coupled to connector ring 316, while the more proximal electrode coils 26, 28, 226, 228 will be coupled to the connector rings 362 and 364. This arrangement will allow the physician to select none, one or both of the move proximal electrode coils. This allows the physician to easily adjust the effective length of the defibrillation electrodes in the coronary sinus/great vein or in the right ventricle at the time implant, or thereafter if the need should arise.

As such, the lead designs described above provide the physician with defibrillation electrode systems which may be corrected, repaired, or tailored to the particular requirements of the patient, at or after implant, without requiring surgical removal of the leads. The electrode systems and their method of use disclosed herein are therefore believed particularly desirable in the context of an implantable defibrillator. However, it is believed that the leads illustrated might also be useful in other contexts.

Further, while all of the embodiments illustrated employ electrode coils, it is within the scope of the invention to employ other forms of electrode surfaces. For example, a plurality of ring-shaped electrodes might be substituted for the multiple electrode coils in the leads illustrated in FIG. 1 through 3. In the context of the leads illustrated in FIGS. 1 and 3, it is anticipated that one or two ring electrodes may be substituted for each of the electrode coils. In the context of the lead illustrated in FIG. 2, it is anticipated that multiple alternating ring electrodes would be required. However, for practical reasons it is believed that the use of electrode coils will the preferred embodiment for practicing the present invention. Similarly, while the embodiments disclosed herein are practiced using particular types of pacing/sensing electrodes and particular connector configurations, these elements have been chosen for the sake of convenience, and may be replaced by any other corresponding electrodes or connectors, or in some cases may be dispensed with entirely. As such, the above disclosure should be considered exemplary, rather than limiting with regard to the following claims.

In conjunction with above disclosure we claim:

1. An implantable transvenous defibrillation lead, comprising:
   an elongated lead body, comprising an elongated insulative sheath and including therein a plurality of mutually insulated conductors.
   an electrical connector assembly mounted to a proximal end of said lead body, said connector assembly provided with a plurality of electrical connectors, each coupled to one of said mutually insulated conductors; and
   an elongated defibrillation electrode comprising a plurality of individual conductive coils exposed to the exterior of said lead body, said individual coils inter-wound to define a multifilar, multi-polar coil, each of said individual coils mutually insulated from one another and coupled to one of said mutually insulated conductors, said multifilar, multi-polar coil extending for a distance of at least four centimeters.

2. A lead according to claim 1 further comprising a pacing electrode, mounted to said lead body and coupled to one of said mutually insulated conductors.

3. A lead according to claim 1 or claim 2 further comprising selector means, coupled intermediate said connector assembly and at least one of said mutually insulated conductors for selectively connecting or disconnecting at least one of said individual coils from one of said electrical connectors on said connector assembly.

4. An implantable transvenous defibrillation lead, comprising:
   an elongated lead body including a elongated insulative sheath and a plurality of mutually insulated electrical conductors mounted therein;
   an electrical connector assembly mounted to a proximal end of said insulative sheath, said connector assembly comprising a plurality of electrical connectors, each of said connectors coupled to one of said mutually insulated conductors;
   an elongated defibrillation electrode comprising a plurality of sequentially arranged, adjacent electrodes, each of said electrodes coupled to one of said mutually insulated conductors; and
   electrode selector means mounted to said lead, for selectively connecting only a first one of said electrodes to said connector assembly and for connecting said first one of said electrodes to said connector assembly along with a second one of said electrodes immediately adjacent to said first electrode, whereby a defibrillation electrode of adjustable length is provided.

5. A lead according to claim 4 wherein said plurality of electrodes includes at least three adjacently arranged electrodes, and wherein said selector means comprises means for selectively connecting only a first one of said electrodes, and for connecting only said first electrode and a second electrode immediately adjacent to said first electrode and for connecting all three of said adjacent electrodes to ones of said electrical connectors on said connector assembly, whereby an adjustable length defibrillation electrode is provided.

6. A method of repairing an implantable defibrillation lead system, comprising:
   inserting a defibrillation lead transvenously into the body of said patient, said defibrillation lead having an elongated defibrillation electrode comprising a plurality of individual coils interwound comprise a multifilar multi-polar coil, each of said coils individually selectable for coupling to an implantable defibrillator;

selectively coupling one or more of said coils to an implantable defibrillator;

detecting a defect in the operation of said electrode system; and correcting said defect by connecting different ones of said individual coils to said defibrillator.

7. A method according to claim 6 wherein said step of inserting said lead comprises inserting said lead into the right ventricle of said patient's heart.

8. A method according to claim 6 wherein said step of inserting said lead comprises inserting said lead into the coronary sinus of said patient's heart.

9. A method for defibrillating a patient's heart, comprising:

transvenously inserting first and second defibrillation leads into the vascular system adjacent the heart of said patient, said first lead provided with a first plurality of adjacent electrodes, each of said first plurality of electrodes mutually insulated from one another, said first lead further comprising means for independently connecting each of said first plurality of electrodes to an implantable defibrillator, said second lead comprising at least a second electrode and means for connecting said second electrode to an implantable defibrillator;

inserting a third defibrillation lead into said patient's body, said third lead also comprising at least a third electrode and means for connecting said third electrode to an implantable defibrillator;

selecting a defibrillator pulse regimen comprising the delivery of a defibrillation pulse between said first and second leads;

electrically connecting less than all of said first plurality of electrodes on said first lead to one another and to said implantable defibrillator, such that those of said first plurality of adjacent electrodes not connected to said implantable defibrillator comprise the electrode or electrodes within said first plurality of electrodes which are located most nearly to said second electrode on said second lead; and delivering a defibrillation pulse between said selected ones of said first plurality of electrodes on said first lead and said second electrode on said second lead.

10. A method according to claim 9 wherein said step of inserting said first and second leads comprises inserting said first and second leads such that one of said first and second defibrillation lead is located in the coronary sinus of said patient's heart and the other of said first and second defibrillation leads is located in the right ventricle of said patient's heart.

11. A method according to claim 9 or claim 10 wherein said step of inserting said third defibrillation lead comprises inserting said third defibrillation lead subcutaneously.

* * * * *